United States Patent
D'Ambrogio et al.

(10) Patent No.: US 8,546,318 B2
(45) Date of Patent: *Oct. 1, 2013

(54) MICROFIBROUS CELLULOSE HAVING A PARTICLE SIZE DISTRIBUTION FOR STRUCTURED SURFACTANT COMPOSITIONS

(75) Inventors: Robert D'Ambrogio, Princeton, NJ (US); Deborah Ann Peru, Lebanon, NJ (US); Joan Ethel Gambogi, Hillsborough, NJ (US); Kevin Mark Kinscherf, Middletown, NJ (US); Dipak Patel, Parsippany, NJ (US); Robert Tavares, Dunellen, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/505,865

(22) PCT Filed: Nov. 4, 2010

(86) PCT No.: PCT/US2010/055421
§ 371 (c)(1),
(2), (4) Date: May 3, 2012

(87) PCT Pub. No.: WO2011/056951
PCT Pub. Date: May 12, 2011

(65) Prior Publication Data
US 2012/0309662 A1    Dec. 6, 2012

Related U.S. Application Data

(60) Provisional application No. 61/257,872, filed on Nov. 4, 2009.

(51) Int. Cl.
*C11D 1/00* (2006.01)
*C11D 3/22* (2006.01)

(52) U.S. Cl.
USPC ........... 510/470; 510/405; 510/418; 510/471; 134/25.2; 134/25.3; 134/39; 134/42

(58) Field of Classification Search
USPC ............... 510/405, 418, 470, 471; 134/25.2, 134/25.3, 39, 42
See application file for complete search history.

(56) References Cited

U.S. PATENT DOCUMENTS

| | | | |
|---|---|---|---|
| 2,785,765 | A | 3/1957 | Cornell |
| 4,018,720 | A | 4/1977 | Lengyel et al. |
| 4,772,425 | A | 9/1988 | Chirash et al. |
| 4,871,251 | A | 10/1989 | Preikschat et al. |
| 4,992,107 | A | 2/1991 | Itoku et al. |
| 5,188,752 | A | 2/1993 | Prencipe et al. |
| 5,252,244 | A | 10/1993 | Beaujean et al. |
| 5,619,043 | A | 4/1997 | Preikschat et al. |
| 5,815,264 | A | 9/1998 | Reed et al. |
| 6,258,771 | B1 | 7/2001 | Hsu et al. |
| 6,274,539 | B1 | 8/2001 | Kacher et al. |
| 6,274,540 | B1 | 8/2001 | Scheibel et al. |
| 6,336,977 | B1 | 1/2002 | Menke et al. |
| 6,380,150 | B1 | 4/2002 | Toussaint et al. |
| 6,449,042 | B1 | 9/2002 | Hamann |
| 6,767,878 | B1 | 7/2004 | Paye et al. |
| 6,940,064 | B2 | 9/2005 | Hamann |
| 7,098,178 | B2 | 8/2006 | Gerke et al. |
| 2003/0109391 | A1 | 6/2003 | Midha et al. |
| 2004/0018950 | A1 | 1/2004 | Foley et al. |
| 2005/0020467 | A1 | 1/2005 | Kinscherf |
| 2007/0010415 | A1 | 1/2007 | Kinscherf et al. |
| 2007/0066507 | A1 | 3/2007 | Fleckenstein et al. |
| 2008/0070823 | A1 | 3/2008 | Gorlin et al. |
| 2008/0108541 | A1 | 5/2008 | Swazey |
| 2008/0108714 | A1 | 5/2008 | Swazey et al. |
| 2008/0146485 | A1 | 6/2008 | Swazey |
| 2008/0242581 | A1 | 10/2008 | Murphy et al. |
| 2009/0105113 | A1 | 4/2009 | Tuzi et al. |
| 2009/0186796 | A1 | 7/2009 | Gomez Ruiz et al. |
| 2010/0150975 | A1 | 6/2010 | Dihora et al. |

FOREIGN PATENT DOCUMENTS

| | | |
|---|---|---|
| WO | WO 2004/071322 | 8/2004 |
| WO | WO 2006/041740 | 4/2006 |
| WO | WO 2007/123566 | 11/2007 |
| WO | WO 2008/076753 | 6/2008 |
| WO | WO 2008/079693 | 7/2008 |
| WO | WO 2009/101545 | * 8/2009 |
| WO | WO 2009/135765 | 11/2009 |

OTHER PUBLICATIONS

Caggioni et al, 2007,"Rheology and microrbcology of a microstructured fluid: The gellan gum case", J. Rheol. 5(15), pp. 851-865.

The Cornell Machine Co, 2004,"Vesator Operation and Process Actions", www.cornellmachine.com/versator_operation_process.htm.

CP Kelco, 2008, "Cellulion™PX microfibrous cellulose blend—prototype formula and FAQs for Liquid Dish Detergents", www.cpkelco.com.

CP Kelco, 2008, "Preparation of Cellulon™ PX microfibrous cellulose blend solutions".

Eiger Torrance Ltd, 2007, "DeAeration Equipment—Versator Product Info", www.eiger-torrance.com/filestore/versator.pdf. created Oct. 2007.

ISR and Written Opinion for PCT/US10/055417 mailed on Feb. 22, 2011.

ISR and Written Opinion for PCT/US10/05541 mailed on Feb. 11, 2011.

(Continued)

*Primary Examiner* — Brian P Mruk
(74) *Attorney, Agent, or Firm* — Michael F. Morgan

(57) ABSTRACT

An aqueous composition comprising surfactant, water, and a suspending agent comprising microfibrous cellulose that is characterized by a particle size distribution of the microfibrous cellulose that provides for increased structuring of the composition to suspend material.

10 Claims, No Drawings

(56) References Cited

OTHER PUBLICATIONS

ISR and Written Opinion for PCT/US10/055424 mailed on Feb. 22, 2011.

Mettler Toledo, 2008, "In-process high-resolution particle microscopy: Process Analytical Technology (PAT)", www.mnt.com/PVM, Lasentec®, PVM®.

Mettler Toledo, 2008, "Particle Characterization:Measure Particle Distribution In-Process; Ensure Targeted Granule Size in Real Time"www.mt.com/fbrmc35.

Mettler Toledo, 2009, "FBRM® (FocusedBeam Reflective Measurement) Technology", http://us.mt.com/us/en/home/supportive_content/ . . . sentec-FBRM-Method-of-Measurement.oneColEd.html.

U.S. Appl. No. 13/505,910, filed May 3, 2012, entitled "Process to Produce Stable Suspending System".

Written Opinion for PCT/US10/055424 mailed on Feb. 14, 2012.

\* cited by examiner

MICROFIBROUS CELLULOSE HAVING A PARTICLE SIZE DISTRIBUTION FOR STRUCTURED SURFACTANT COMPOSITIONS

CROSS REFERENCE TO RELATED APPLICATIONS

This application is a national stage entry under 35 U.S.C. §371 of International Patent Application No. PCT/US2010/055421, filed 4 Nov. 2010, which claims priority to U. S. Provisional Patent Application No. 61/257,872, filed on 4 Nov. 2009, which is incorporated herein by reference.

BACKGROUND

Structured liquids are known in the art for suspending materials such as beads in liquid cleaning compositions. The methods of providing structure to the liquid includes using particular surfactants to structure the liquid, or by the addition of suspending agents such as polysaccharides, natural gums, or cellulose, that enable the liquid to suspend materials therein for long periods of time. These suspended materials can be functional, non-functional (aesthetic) or both. By aesthetic it is meant that the suspended materials impart a certain visual appearance that is pleasing or eye catching. By functional it is meant that the suspended materials contribute to the action of the composition in cleaning, fragrance release, shine enhancement, or other intended action of the composition.

BRIEF SUMMARY

An aqueous composition comprising
a) a surfactant;
b) a suspending agent comprising microfibrous cellulose; and
c) water,
wherein the composition is characterized by focused beam reflectance method having at least one of the following:
(i) less than 80 counts per second in a 50-100 micron no weight range,
(ii) less than 15 counts per second in a 100-150 micron no weight range,
(iii) less than 100 counts per second in a 46-158 micron no weight range,
(iv) less than 10 counts per second in a 147-316 micron no weight range,
(v) less than 1 count per second in a 293-500 micron no weight range,
(vi) a value less than 20 for no weight median in a 9-300 micron range,
(vii) a value less than 25 for no weight mean in a 9-300 micron range.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The ability of microfibrous cellulose (MFC) to form a structured surfactant composition can be increased by forming a particle size distribution of the fibers. First, MFC is added to water along with an optional preservative to form a 1 weight % mixture of MFC in water. This composition is mixed until a homogeneous dispersion is formed. The dispersion is then passed through a high sheer device, such as a variable pressure homogenizer or rotor-stator homogenizer, to sheer the particles to increase the surface area of the particles. The selection of the homogenizer and its process conditions leads to the particle size that is achieved.

In one embodiment, the homogenizer is from APV Homogenizer Group of Lake Mills, Wis. For pilot scale, model 15MR-8TA can be used. For commercial scale, model 24MR can be used. These devices are set for 55,158,058 Pa (8000 psi). Using this homogenizer at this setting will provide the particle size distribution.

This particle size distribution allows the MFC to provide the desired level of yield stress to the composition to suspend material.

The particle size is measured using a Focus Beam Reflectance Method (FBRM), which is described below.

Once the dispersion is processed to have the particle size distribution, it can then be mixed into a surfactant composition by any mixing method to structure the surfactant composition.

Measuring the Size of MFC Particles

The particle size of MFC particles can be measured using particle Focused Beam Reflectance Measurement (FBRM). This device can be obtained from Mettler-Toledo of Columbia, Md. as FBRM Model S 400. The FBRM instrument involves the use of a beam of laser light focused on the outside of a sapphire window. The beam is rotated at a constant speed of 2 m/s and the laser energy is reflected back into the probe by backscatter from particles on or close to the sapphire window. The duration of the backscatter is measured and represented as a particle chord length. The measured chord lengths are counted, categorized and displayed as a distribution curve or as a trend of selected size ranges. The chord lengths may be represented as non-weighted, linear, square or cube-weighted distributions.

The sample is centrifuged to remove air bubbles from the sample. The regions from 50-100 microns and 45-150 microns are sensitive to remaining air bubbles. The range 46-158 microns is sensitive to bubbles and varies greatly between aerated and un-aerated samples. When split into two ranges, 50-100 micron and 100-150 micron, the 50-100 range is populated by bubbles while the 100-150 micron range show intrinsic characteristics of the premix.

The following procedure is used to analyze a sample for particle size. When the particle size of MFC is described throughout this specification and in the claims, this procedure is used for measuring.

Apparatus

Mettler-Toledo Focus Beam Reflective Method (FBRM) Model S 400
Computer:
iC FBRM 4.0 software
100 ml glass beakers
236.6 ml (8 oz.) ointment jars
Mettler-Toledo Static beaker stand and mixer
IEC Model K Centrifuge 1 Starting up a New Experiment
   1.1 Turn on FBRM instrument power and computer. Allow the FBRM to sufficiently heat up before using. The yellow light on the front of the FBRM marked temp will be lit while the machine is heating up.

1.2 Double click to launch the iC FBRM 4.0 software.
1.3 Select New Experiment.
1.4 An Experiment Schedule is created. For the default method, there is a single phase with duration of 8 hours with a sampling interval of 10 seconds. Click Next when finished.

2 Sample Preparation
2.1 Fill an 8 oz. ointment jar ¾ full with sample to be measured. Place jar in IEC centrifuge at 25,000 rpm for 35 minutes to remove air from the sample.
2.2 Using a spoon, skim off the top layer of sample from the jar containing foam bubbles. Replace into centrifuge at 25,000 rpm for 20 minutes and re-skim the sample again.
2.3 Pour about 80 ml of the sample into a 100 ml glass beaker.
2.4 Place the beaker on the fixed beaker stand and turn on the IKA mixer to the marked 400 rpm.
2.5 The instrument is inserted into the solution.

3 Collecting Data on the FBRM Software
3.1 Push the Play Button on the upper left to begin collecting data.
3.2 In the Toolbox area on the right hand side, under Data Treatments, averaging and channeling grouping of the data can be changed. For the given method, averaging is enabled, and set to a moving average with a window size of 3. Channel grouping is a low resolution, with log spacing, and a range of 1-1000 μm.

4 Viewing the Statistical Data
4.1 The data is shown in spreadsheet form in the Statistics area on the right half of the screen.

In one embodiment, the composition is characterized by focused beam reflectance method having at least one of the following:
(i) less than 80 counts per second in a 50-100 micron no weight range,
(ii) less than 15 counts per second in a 100-150 micron no weight range,
(iii) less than 100 counts per second in a 46-158 micron no weight range,
(iv) less than 20 counts per second in a 147-316 micron no weight range,
(v) less than 10 counts per second in a 293-500 micron no weight range,
(vi) a value less than 20 for no weight median in a 9-300 micron range,
(vii) a value less than 25 for no weight mean in a 9-300 micron range.

In one embodiment, the composition is characterized by each of (i) to (v). In another embodiment, the composition is characterized by each of the above. No weight refers to no statistical weighting of the results, and it emphasizes accuracy in the small size range. In one embodiment, the counts for the ranges in the 150-500 micron range should be minimized. The composition can be tested before or after pasteurization, and the ranges apply to either. It is preferred to test after pasteurization because the 50-100 micron range and the 48-158 micron range can be sensitive to any air bubbles in the composition, which are removed during pasteurization.

Suspending Agents

Suspending agents are any material that increases the ability of the composition to suspend material. The suspending agent of this invention comprises microfibrous cellulose.

The suspending agent can include an additional suspending agent. Examples of an additional suspending agent include, but are not limited to, gums, gellan gum, polymeric gums, polysaccharides, pectine, alginate, arabinogalactan, carageenan, xanthum gum, guar gum, rhamsan gum, furcellaran gum, celluloses, and carboxymethylcellulose.

The amount of suspending agent can be any amount that provides for a desired level of suspending ability. In one embodiment, the suspending agent is present in an amount from 0.01 to 10% by weight of the composition.

In one embodiment, the microfibrous cellulose is present in the composition in an amount of 0.01 to 0.12 weight %. In other embodiments, the amount is at least 0.02, 0.03, 0.04, 0.05, 0.06, 0.07, 0.08, 0.09, 0.1 up to 0.12 weight %. In one embodiment, the amount is 0.048 weight %.

In one embodiment, the suspending agent is a combination of microfibrous cellulose (MFC), xanthan gum, and carboxymethyl cellulose (CMC). This suspending agent is available from CP Kelco as Cellulon™ PX or Axcel™ CG-PX. It is a 6:3:1 blend by weight of MFC:xanthan gum:CMC. It is further described in United States Patent Publication Nos. 2008/0108714A1, 2008/0146485A1, and 2008/0108541A1. On addition of water, the xanthan gum and CMC become hydrated and provide for better dispersion of MFC. In one embodiment, the MFC:xanthan gum:CMC is present in the composition in an amount of 0.01 to 0.2 weight %. In other embodiments, the amount is at least 0.02, 0.03, 0.04, 0.05, 0.06, 0.07, 0.08, 0.09, 0.1, or 0.15 up to 0.2 weight %. In one embodiment, the amount is 0.08 weight %.

Liquid Portion

The composition contains at least one surfactant. In certain embodiments, the surfactant is present in an amount that is at least 1% by weight of the composition based on the active amount of the surfactant. In other embodiments, the amount of surfactant is at least 5, 10, 20, 25, 30, 35, or 40% by weight. In another embodiment, the amount of surfactant is 1% to 45% by weight. The surfactant can be any surfactant or any combination of surfactants. Examples of surfactants include anionic, nonionic, cationic, amphoteric, or zwitterionic. For a list of surfactants and other materials that can be included in the composition, see United States Patent Publication No. 2007/0010415A1.

Water is included in the composition. The amount of water is variable depending on the amounts of other materials added to the composition.

The composition can be formulated to be any type of liquid cleansing composition. The composition can be used as a light duty liquid (LDL) dish detergent, hand soap, body wash, or a laundry detergent. One embodiment will be for a dish detergent.

In another embodiment, the composition can be degassed after the suspending agent is mixed with the surfactant and before suspended material is added. For further information, see U.S. Application No. 61/257,885 filed on 4 Nov. 2009 entitled "PROCESS TO PRODUCE STABLE SUSPENDING SYSTEM", which is incorporated herein by reference in its entirety. In another embodiment, an alkaline earth metal ion is included with the microfibrous cellulose to increase the yield stress to increase the suspending ability. For further information, see U.S. Application No. 61/257,940 filed on 4 Nov. 2009 entitled "MICROFIBROUS CELLULOSE AND ALKALINE EARTH METAL ION STRUCTURED SURFACTANT COMPOSITION", which is incorporated herein by reference in its entirety.

The compositions can be made by simple mixing methods from readily available components which, on storage, do not adversely affect the entire composition. Mixing can be done by any mixer that forms the composition. Examples of mixers include, but are not limited to, static mixers and in-line mixers.

Suspended Materials

Once the composition is structured with a suspending agent, the composition can suspend suspended materials. Suspended materials are defined as water insoluble visible particles. They can be functional or non-functional (aesthetic), i.e. functional materials have components that augment the performance capabilities of the product and non-functional materials are present solely for aesthetic purposes. Functionality can often be provided by encapsulating materials that deliver functional benefits or by providing a tactile benefit (e.g. scrubbing). Functional materials, however, may also have aesthetic purposes.

The suspended material can be density matched to the liquid portion if very low viscosity is desired. Density matched means that the density of the suspended material is close to the density of the liquid portion so that the suspended material remains suspended. In one embodiment, the density of the suspended material has a density that is 97% to 103% of the density value of the liquid portion. In other embodiments, the suspend material is not density matched.

At least a portion of the suspended material is of any size that is viewable by a person. By viewable it is meant that the suspended material can be seen by a non-color blind person with an unaided eye at 20/20 or corrected to 20/20 with glasses or contact lenses at a distance of 30 cm from the composition under incandescent light, florescent light, or sunlight. In other embodiments, at least 50%, at least 60%, at least 70%, at least 80%, at least 90%, at least 95%, or at least 99% of the particles are viewable by a person. In one embodiment, the particle size is 100 to 2500 microns in a longest dimension of the suspended material. In another embodiment, the particle size is 250 to 2250 microns. In another embodiment, the particle size is 500 to 1500 microns. In another embodiment, the particle size is 700 to 1000 microns. In another embodiment, a combination of more than one particle sizes can be used.

The suspended material can have any shape. Examples of shapes include, but are not limited to, spherical, polyhedral, cubic, box, tetrahedral, irregular three dimensional shapes, flat polygons, triangles, rectangles, squares, pentagons, hexagons, octagons, stars, characters, animals, plants, objects, cars, or any other desired shape.

The suspended material can be present in any amount in the composition that allows the suspended material to remain suspended. In one embodiment, the suspended material is present in an amount of 0.01 and 10% by weight of the total composition.

The suspended material can be selected to be of one size and one shape, one size and a combination of shapes, a combination of sizes and one shape, or a combination of sizes and a combination of shapes. Also, the color of the suspended material can be varied along with the size and/or shape. Mixtures of suspended materials that vary by size, shape, and/or color can be used to communicate different attributes that the product can deliver to a consumer.

The suspended material can be functional, non-functional (aesthetic), or a combination of both. They can be made from a variety of materials such as the following non-limiting examples: gelatin, cellulose, agar, waxes, polyethylene, and insoluble inorganic materials like silica and calcium carbonate. The material may also have an encapsulate core containing hydrophobic compounds and mixtures such as these non-limiting examples: aloe, vitamins, essential oils, natural oils, solvents, esters, or any fragrance ingredient. These materials may be density matched by encapsulating oils or other materials that help make the density of the suspended material equal to that of the bulk composition. Alternatively, they may be made porous in a way that allows the liquid portion to diffuse into the suspended material in a manner that is self density matching. Density matching produces compositions that can suspend material at a viscosity less than 1500 mPas. Also, the particles may be non-density matched, that is being either less or more dense than the composition. In these compositions, the liquid portion can be designed to have a yield stress to aid in the stabilization of suspended material.

Viscosity

The composition has a viscosity that allows the composition to be pourable. In certain embodiments, the viscosity is below 10,000 mPas. Viscosity is measured using a Brookfield RVT Viscometer using spindle 21 at 20 RPM at 25° C. In one embodiment, the viscosity is less than 5,000 mPas. In other embodiments, the viscosity is less than 1,500 mPas, less than 1,000 mPas, less than 750 mPas, or less than 500 mPas.

The yield stress is measured on a TA Instruments ARG2 controlled stress rheometer utilizing a small vane (15 mm diameter) geometry and 30 mm jacketed sample cup at 25° C. with a 10,000 gm gap. A conditioning step is programmed into the creep test—after loading the sample, a two minute "relaxation" period is used in which the sample is equilibrated to 25° C. before measurements are started. The 25° C. temperature is maintained by the instrument throughout the test. Yield stress was determined utilizing a sequential creep test method. In this test, to ensure reproducibility, samples were equilibrated in a sequence of four identical stress/relaxation steps at the lowest initial stress of 0.01 Pa. Once the sample was equilibrated, a further series of stress/relaxation steps were conducted with gradually increasing applied stress until the resulting plot on creep compliance vs. time graph shows an upward curvature. At this time, the test was stopped and the stress at which the bend occurs is taken as the "yield stress". The yield stress is measured with any suspended material present. When suspended material is present, the gap is selected to provide sufficient clearance so as not to interfere with the suspended material. The 10,000 μm gap is sufficient for suspended material having a particle size up to 2,000 μm.

Stability of the Composition

When a structured surfactant composition has been degassed prior to the addition of suspended material, the effect is that the composition maintains a stable suspending system over time. This can be measured by the yield stress of the composition. Over time, the yield stress is maintained. In one embodiment, the yield stress does not decrease by more than 20% of its value over a 3 month period. In other embodiments, the period of time is at least 4, 5, 6, 7, 8, 9, 10, 12, or 18 months. In one embodiment, the drop in yield stress is less than 10% over any of the previously listed periods of time. The yield stress is measured at an initial time and then after the given period of time.

In one embodiment, the composition has a yield stress that is at least 0.3 Pa. In other embodiments, the yield stress is at least 0.5, 0.6, 0.7, 0.8, 0.9, or 1 Pa. For most suspended material, a yield stress of up to 1.5 Pa is sufficient. In other embodiments, the yield stress is 0.3 to 1.5 Pa. In other embodiments, the yield stress is 0.5 to 1.5 Pa.

Measuring the Amount of Gas in a Composition

The amount of gas in a composition can be measured using particle video microscopy. This device can be obtained from Mettler-Toledo of Columbia, Md. as Lasentec™ V819 with PVM™ technology. For more information on this device, see U.S. Pat. Nos. 4,871,251; 5,815,264; 5,619,043; 6,449,042; and 6,940,064.

The following procedure is used to analyze a sample of material for gas bubble content. When the gas bubble content is described throughout this specification and in the claims, this procedure is used for measuring.

1. Apparatus
   Mettler Toledo Lasentec® V819 Particle Video Microscope (PVM)
   PVM V819 Version 9.2.0 IB4 software
   400 ml glass beakers
   Mettler Toledo Static beaker stand
   IKA Eurostar Power Control-Visc Homogenizer Model CV81 (rpm range 50-2000)
   The PVM is equipped with a polytetrafluoroethylene reflection cap on the tip of the instrument, and the PVM is equipped with the optional backscatter laser to increase viewability.
2. Procedure
   2.1. Operation of Mettler Toledo PVM Microscope
      2.1.1. Turn on PVM instrument power and computer. Wait 30 seconds for the instrument and computer to begin communication. Double click to launch the PVM On-Line Image Acquisition software.
      2.1.2. Select Image Analysis/Algorithms/Blob Analysis. Press the green Go button. The Blob Analysis window has 6 parameters that need to be adjusted to properly focus on the bubbles. The measurement settings are adjusted according to the specifications found in Table 1. Default settings should be used for the following: Preprocessing—Edge Filter Sobel; Output Distribution—Diameter (Spherical Eq); Delta 1 Input—Avg. Aspect Ratio; Image Analysis Window—Show Detected Particles Enabled; Overlay Result—Original Image.

TABLE 1

PVM Measurement Settings for Structured LDL

| Threshold | | Preprocessing | | Particle acceptance criteria | | Instrument Settings | |
|---|---|---|---|---|---|---|---|
| Lower | Upper | Decimation Factor | Filter Type | Min Pixel Size | Reject particles w/ ellipsoidity less than size | Gain | Laser On |
| 2 | 50 | 2 | 5 × 5 | 50 | 60 | 50 | 6 |

2.1.3. Click on the Settings/Instrument Settings button. Set the Image Acquisition Gain between 50-55 and select Illumination Settings and set to Laser 6 only and Laser Intensity to 100.
   2.2. Operation of PVM Acquisition Software
      2.2.1. Once the parameters for the PVM camera have been optimized, double click to launch the Lasentec PVM Stat Acquisition 6.0 Build 11 software.
      2.2.2. Within the software, create a new file to save new data by clicking the Open file for Save button. Type in the name of the file to save.
      2.2.3. Click the Setup Menu/Stat. Config/Load Stats.Config button. Select the statistical analysis file that contains the specifications. This allows for a comparison between the real time data and the acceptable specification for the product. This step is optional.
      2.2.4. Press the Measuring Press to Stop Button to begin viewing the bubble distribution data.
      2.2.5. To begin collecting data, click the Not Saving Press to Autosave button.
   2.3. Sample Preparation
      2.3.1. Pour 200 ml of the sample into a glass beaker.
      2.3.2. Place the beaker on the fixed beaker stand. Also be sure that the PVM probe has a polytetrafluoroethylene reflection cap on the tip to enhance the backscattered laser light back to the detector. Manual twist the IKA impeller to be sure the impeller moves freely inside the beaker and does not hit the probe or polytetrafluoroethylene cap.
      2.3.3. Turn on the IKA homogenizer and adjust the RPM to between 160-170 RPM for Premix and finished product analysis. This RPM will provide a good agitation to move product through the probe without introducing bubbles into the sample. Note: always be sure the IKA homogenize is at the lowest RPM when it is turned on to avoid introducing bubbles into the sample.
3. Analysis
   3.1. Post Analysis of Data Using PVM Sequence Review Software
      3.1.1. To analyze data after acquisition, double click on the Lasentec FBRM Data Review 6.0 Build 11 to launch the software.
      3.1.2. Within the software, click on the Setup menu/Open File button and find/open the file that contains the data to be reviewed.
      3.1.3. Click on the Setup Menu/Stat Config. Button and select the Load Stats Config file for the application of interest.
   3.2. No calculations are required beyond what is provided in the Statistical Configuration used in the PVM Sequence Review software. During data collection and post data review, the channel grouping is fixed at 0-500 micron 100 linear in measurement range of 0-1000 micron. The Channel grouping gives the user the ability to group the primary. distribution into channels that are more appropriate for the application of interest. Square weighting generally is used to analyze particle in the large size range; whereas, No weighting is used to analyze particles in the small size range. The typical distributions used to evaluate the bubble content are shown in the table below.

| 25-145 | 10-45 micron | 45-80 micron | 80-140 micron | 140-200 micron | 200-500 micron |
|---|---|---|---|---|---|
| Median | counts/sec | counts/sec | counts/sec | counts/sec | counts/sec |

In one embodiment, an amount of air bubbles after degassing is less than 10 counts per second in at least one of the above particle size ranges according to the Gas Bubble Test. In other embodiments, the count is less than 9, less than 8, less than 7, less than 6, less than 5, less than 4, less than 3, less than 2, or less than 1 count per second. In one embodiment, the count is less than 2 counts per second. In other embodiments, the count is less than 10, or 9, or 8, or 7, or 6, or 5, or 4, or 3, or 2, or 1 in each of the particle size ranges. The above counts per second ranges apply to both linear channel measurement and log channel measurement on the apparatus.

In one embodiment, the composition has, as measured on a linear channel, the following counts:

| 10-45 micron | 45-80 micron | 80-140 micron | 140-200 micron | 200-500 micron |
|---|---|---|---|---|
| <6.2 counts/sec | <7.3 counts/sec | <3.7 counts/sec | <0.32 counts/sec | about 0 counts/sec. |

In one embodiment, the composition has, as measured on a log channel, the following counts:

| 10-45 micron | 45-80 micron | 80-140 micron | 140-200 micron | 200-500 micron |
|---|---|---|---|---|
| <1 counts/sec | <3.4 counts/sec | <5.5 counts/sec | <4.6 counts/sec | <1 counts/sec. |

After degassing, it is recommended for any transport of the composition before it is packaged that the transport occur with equipment that avoids reaeration of the composition. Positive displacement pumps are one type of pump that can be used to transport the composition to packaging. These pumps avoid cavitation, which can entrain air.

Specific Embodiments of the Invention

Below are compositions that can be used in the process. Amounts are based on active weight of the material.

| Material | Weight % |
|---|---|
| C12-15 Alcohol EO1.3:1 ammonium sulfate | 0-20 |
| Mg Dodecyl Benzene Sulfonate | 0-15 |
| Lauramidopropyldimethylamine Oxide | 0-10 |
| Na Dodecyl Benzene Sulfonate | 0-10 |
| Ethanol | 0-6 |
| Sodium Xylene Sulfonate | 0-5 |
| Myristamidopropylamine Oxide | 0-5 |
| Pentasodium Pentatate | 0-0.5 |
| PPG-20 Methyl Glucose Ether | 0-0.1 |
| Gellan Gum | 0 |
| MFC:xanthan gum:CMC (6:3:1) | 0.01-0.2 |
| Water, fragrance, and preservatives | QS |
| Suspended Material | 0.05-10 |
| pH | 6-8 |
| Viscosity | 300-1000 |
| Yield Stress | >0.25 |

What is claimed is:

1. A method for making an aqueous composition comprising
   (I) processing an aqueous composition comprising a suspending agent comprising microfibrous cellulose in a homogenizer,
   (II) measuring particle size of the suspending agent by Focused Beam Reflectance Measurement, and
   (III) mixing a surfactant into the aqueous composition.

2. The method of claim 1, wherein the suspending agent is processed until the suspending agent particle size is characterized by at least one of the following according to the Focused Beam Reflectance Measurement:
   (i) less than 80 counts per second in a 50-100 micron no weight range,
   (ii) less than 15 counts per second in a 100-150 micron no weight range,
   (iii) less than 100 counts per second in a 46-158 micron no weight range,
   (iv) less than 20 counts per second in a 147-316 micron no weight range,
   (v) less than 10 counts per second in a 293-500 micron no weight range,
   (vi) a value less than 20 for no weight median in a 9-300 micron range, and
   (vii) a value less than 25 for no weight mean in a 9-300 micron range.

3. The method of claim 1, wherein the suspending agent comprises a mixture of microfibrous cellulose, xanthan gum, and carboxymethyl cellulose.

4. The method of claim 1, wherein the suspending agent comprises a 6:3:1 blend by weight of microfibrous cellulose: xanthan gum: carboxymethyl cellulose.

5. The method of claim 1, wherein the composition is a light duty dish liquid containing at least 15 weight % surfactant.

6. The method of claim 1 further comprising suspended material.

7. The method of claim 1, wherein the composition has a gas bubble content of less than 10 counts per second in at least one of the following particle size ranges according to the Gas Bubble Test:
   (i) 10 to 45 microns,
   (ii) 45-80 microns,
   (iii) 80-140 microns,
   (iv) 140-200 microns, and
   (v) 200-500 microns.

8. The method of claim 7, wherein the composition has a gas bubble content of less than 10 counts per second in all of the ranges.

9. The method of claim 6, wherein the suspended material is not density matched to the composition.

10. The method of claim 1, wherein the composition is characterized by Focused Beam Reflectance Measurement having each of the following:
    (i) less than 80 counts per second in a 50-100 micron no weight range,
    (ii) less than 15 counts per second in a 100-150 micron no weight range,
    (iii) less than 100 counts per second in a 46-158 micron no weight range,
    (iv) less than 20 counts per second in a 147-316 micron no weight range, and
    (v) less than 10 counts per second in a 293-500 micron no weight range.

* * * * *